US007235368B2

(12) United States Patent
Bergmann et al.

(10) Patent No.: US 7,235,368 B2
(45) Date of Patent: Jun. 26, 2007

(54) CHP FOR USE AS MARKER FOR SEPSIS-TYPE INFLAMMATORY DISEASES

(75) Inventors: Andreas Bergmann, Berlin (DE); Joachim Struck, Berlin (DE); Monika Ühlein, Berlin (DE)

(73) Assignee: B.R.A.H.M.S Aktiengesellschaft, Hennigsdorf (DE)

( * ) Notice: Subject to any disclaimer, the term of this patent is extended or adjusted under 35 U.S.C. 154(b) by 0 days.

(21) Appl. No.: 10/480,847

(22) PCT Filed: Jun. 17, 2002

(86) PCT No.: PCT/EP02/06660

§ 371 (c)(1),
(2), (4) Date: Jun. 4, 2004

(87) PCT Pub. No.: WO03/005035

PCT Pub. Date: Jan. 16, 2003

(65) Prior Publication Data

US 2005/0064409 A1 Mar. 24, 2005

(30) Foreign Application Priority Data

Jul. 2, 2001 (DE) .............................. 101 31 922

(51) Int. Cl.
*G01N 33/53* (2006.01)
(52) U.S. Cl. .................. 435/7.1; 435/7.94; 435/7.95; 436/15; 436/64; 436/86; 436/173
(58) Field of Classification Search ................ 436/15, 436/64, 86, 173, 7.1; 435/7.93, 7.94, 7.95
See application file for complete search history.

(56) References Cited

U.S. PATENT DOCUMENTS

| 5,639,617 A | 6/1997 | Bohuon ..................... 435/7.1 |
| 5,660,994 A | 8/1997 | Bruder-Heid et al. ...... 435/7.23 |

FOREIGN PATENT DOCUMENTS

| DE | 198 47 690 A1 | 4/2000 |
| EP | 0 656 121 B1 | 3/1998 |
| WO | WO 99/37790 | 7/1999 |
| WO | WO 00/12120 | * 3/2000 |
| WO | WO 00/22439 | 4/2000 |

OTHER PUBLICATIONS

Wei et al. WO 00/12120 English Translation.*
Biochemistry 1990 vol. 29, p. 8509 (Wells et al.) From genes to proteins structure and functions in Trends in Biotech 2000, vol. 18, p. 34 (Skolnick); (Tobias et al.) "Errors in genome annotation." In Trends in Genetics vol. 15, p. 132 (Brenner et al.).*
"The Protein Folding Problem and Tertiary Structure Prediction, Chapter 14: Computational Complexity Protein Structure Prediction, and the Levinthal Paradox" pp. 492-495.*
"Powers and Pitfalls in Sequence Analysis" in Trend in Genetics vol. 14, p. 398 (Bork et al).; "Go hunting in sequence databases but watch out for the traps" in Trends in Genetics, vol. 12, p. 425 (Bork).*
Assicot, et al., "High Serum Procalcitonin Concentrations in Patients with Sepsis and Infection," *Lancet*, 341(8844):515-518, 1993.
Beishuizen et al., "Endogenous Mediators in Sepsis and Septic Shock," *Advances Clin. Chem.*, 33:55-131, 1999.
Calandra et al., "Protection from Septic Shock by Neutralization of Macrophage Migration Inhibitory Factor," *Nature Medicine*, 6(2):164-170, 2000.
Gabay and Kushner, "Acute-Phase Proteins and Other Systemic Responses to Inflammation," *New Engl. J. Med.*, 340(6):448-454, 1999.
Garber, "Protein C May Be Sepsis Solution," *Nature Biotechnology*, 18:917-918, 2000.
Ghillani et al., "Monoclonal Antipeptide Antibodies as Tools to Dissect Closely Related Gene Products," *J. Immunol.*, 141(9):3156-3163, 1988.
Ghillani et al., "Identification and Measurement of Calcitonin Precursors in Serum of Patients with Malignant Diseases," *Cancer Research*, 49(23):6845-6851, 1989.
Kanazawa et al., "CYFRA 21-1. A Cytokeratin Subunit 19 Fragment, in Bronchoalveolar Lavage Fluid from Patients with Interstitial Lung Disease," *Clin. Sci.*, 94(5):531-539, 1998.
Klose, "Fractionated Extraction of Total Tissue Proteins from Mouse and Human for 2-D Electrophoresis," In: *Methods in Molecular Biology*, vol. 112, *2-D Proteame Analysis Protocols*, Humana Press Inc., N.J., pp. 67-85.
Klose and Kobalz, "Two-Dimensional Electrophoresis of Proteins: An Updated Protocol and Implications for a Functional Analysis of the Genome," *Electrophoresis*, 16:1034-1059, 1995.
Lin et al., "Inhibition of Calcineurin Phosphatase Activity by a Calcineurin B Homologous Protein," *J. Biol. Chem.*, 274(51):36125-36131, 1999.
Lingner et al., "Reverse Transcriptase Motifs in the Catalytic Subunit of Telomerase," *Science*, 276:561-567, 1997.
Mann and Pandey, "Use of Mass Spectrometry-Derived Data to Annotate Nucleotide and Protein Sequence Databases," *TRENDS Biochem. Sci.*, 26(1):54-61, 2001.
Neubauer et al., Mass Spectrometry and EST-Database Searching Allows Characterization of the Multi-Protein Spliceosome Complex, *Nature Genetics*, 20:46-50, 1998.
Oczenski et al., "Procalcitonin: A New Parameter for the Diagnosis of Bacterial Infection in the Peri-Operative Period," *Eur. J. Anaesthesiol.*, 15:202-209, 1998.

(Continued)

*Primary Examiner*—Long V. Le
*Assistant Examiner*—Jacob Cheu
(74) *Attorney, Agent, or Firm*—Heslin Rothenberg Farley & Mesiti P.C.; Kathy Smith Dias, Esq.

(57) ABSTRACT

Use of calcineurin B homologous protein (CHP) from body fluids or body tissues as a marker peptide for diagnosis, for prognosis and for monitoring the course of inflammations and infections and/or as a target for therapeutically influencing the course of inflammations and/or infections.

3 Claims, 2 Drawing Sheets

OTHER PUBLICATIONS

Otto et al., "Identification of Human Myocardial Proteins Separated by Two-Dimensional Electrophoresis Using an Effective Sample Preparation for Mass Spectrometry," *Electrophoresis*, 17:1643-1650, 1996.

Panacek, "Anti-TNF Strategies," *Intensive Care Med.*, 23:1144-1149, 1997.

Redl et al., "Procalcitonin Release Patterns in a Baboon Model of Trauma and Sepsis: Relationship to Cytokines and Neopterin," *Crit. Care Med.*, 28(11):3659-3663, 2000.

Redl and Schlag, "Non-Human Primate Models of Sepsis," *Sepsis*, 2:243-253, 1998.

Reinhart et al., "Sepsis Und Spetischer Schcok," *Intensivmedizin*, 756-760, 2001.

International Search Report for PCT/EP 02/06660, mailed Oct. 10, 2002.

Aird, "The Hematologic System as a Marker of Organ Dysfunction in Sepsis," *Mayo Clin, Proc.*, 78:869-881, 2003.

Carrigan et al., "Toward Resolving the Challenges of Sepsis Diagnosis," *Clin. Chem.*, 50(8):1301-1314, 2004.

Hotchkiss and Karl; "The Pathophysiology and Treatment of Sepsis," *N. Engl. J. Med.*, 348(2):138-150, 2003.

Marshall et al., "Measures, Markers, and Mediators: Toward a Staging System for Clinical Sepsis. A Report of the Fifth Toronto Sepsis Roundtable, Toronto, Ontario, Canada, Oct. 25-26, 2000," *Crit. Care Med.*, 31(5):1560-1567, 2003 (Abstract only).

Oberholzer et al., "Sepsis Syndromes: Understanding the Role of Innate and Acquired Immunity," *Shock*, 16(2):83-96, 2001 (Abstract only).

\* cited by examiner

CHP FOR USE AS MARKER FOR SEPSIS-TYPE INFLAMMATORY DISEASES

The present application is a nationalization of PCT Application Ser. No. PCT/EP02/06660, filed Jun. 17, 2002, which claims priority to German priority application Ser. No. 101 31 922.3, filed Jul. 2, 2001.

The present invention relates to novel uses of the so-called calcineurin B homologous protein (CHP) for the medical diagnosis and therapy of inflammatory diseases and sepsis. It is based on the detection for the first time of greatly increased concentrations of CHP in liver tissue of primates in which a sepsis or systemic inflammation is caused experimentally by toxin administration.

The present invention has its origin in intensive research work by the Applicant in relation to further improvements of the diagnosis and therapy of inflammations and infections, in particular of inflammations of infectious aetiology and sepsis.

Inflammations are defined very generally by certain physiological reactions of an organism to different types of external effects, such as, for example, injuries, burns, allergens, infections by microorganisms, such as bacteria and fungi and viruses, to foreign tissues which trigger rejection reactions, or to certain inflammatory endogenous conditions of the body, for example in autoimmune diseases and cancer. Inflammations may occur as harmless, localized reactions of the body but are also typical features of the numerous serious chronic and acute diseases of individual tissues, organs, organ parts and tissue parts.

Local inflammations are generally part of the healthy immune reaction of the body to harmful effects and hence part of the life-preserving defence mechanism of the body. If, however, inflammations are part of a misdirected reaction of the body to certain endogenous processes, such as, for example, in autoimmune diseases, and/or are of a chronic nature, or if they achieve a systemic extent, as in the case of systemic inflammatory response syndrome (SIRS) or in the case of a severe sepsis caused by infection, the physiological processes typical of inflammatory reactions go out of control and become the actual, frequently life-threatening pathological process.

It is now known that the origin and the course of inflammatory processes are controlled by a considerable number of substances which are predominantly of a protein or peptide nature or are accompanied by the occurrence of certain biomolecules for a more or less limited time. The endogenous substances involved in inflammatory reactions include in particular those which may be counted among the cytokines, mediators, vasoactive substances and acute phase proteins and/or hormonal regulators. The inflammatory reaction is a complex physiological reaction in which both the endogenous substances activating the inflammatory process (e.g. TNF-$\alpha$) and deactivating substances (e.g. interleukin-10) are involved.

In systemic inflammations, as in the case of a sepsis or of septic shock, the inflammation-specific reaction cascades spread in an uncontrolled manner over the whole body and become life-threatening in the context of an excessive immune response. Regarding the current knowledge about the occurrence and the possible role of individual groups of endogenous inflammation-specific substances, reference is made, for example, to A. Beishuizen et al., "Endogenous Mediators in Sepsis and Septic Shock", Advances in Clinical. Chemistry, Vol. 33, 1999, 55–131; and C. Gabay et al., "Acute Phase Proteins and Other Systemic Responses to Inflammation", The New England Journal of Medicine, Vol. 340, No. 6, 1999, 448–454. Since the understanding of sepsis and related systemic inflammatory diseases, and hence also the recognized definitions, have changed in recent years, reference is also made to K. Reinhart et al., "Sepsis und septischer Schock" [Sepsis and septic shock], in: Intensivmedizin, Georg Thieme Verlag, Stuttgart, New York, 2001, 756–760, where a modern definition of sepsis is given. In the context of the present application, the terms sepsis and inflammatory diseases used are based on the definitions given in the stated three references.

Whereas at least in Europe the systemic bacterial infection detectable by a positive blood culture long characterized the term sepsis, sepsis is now primarily understood as being systemic inflammation which is caused by infection but, as a pathological process, has great similarities to systemic inflammations which are triggered by other causes. Said transformation in the understanding of sepsis has resulted in changes in the diagnostic approaches. Thus, the direct detection of bacterial pathogens was replaced or supplemented by complex monitoring of physiological parameters and, more recently, in particular by the detection of certain endogenous substances involved in the sepsis process or in the inflammatory process, i.e. specific "biomarkers".

Of the large number of mediators and acute phase proteins which are known to be involved in an inflammatory process, the ones which are suitable for diagnostic purposes are in particular those whose occurrence is very specific for inflammatory diseases or certain phases of inflammatory diseases, whose concentrations change in a dramatic and diagnostically significant manner and which moreover have the stabilities required for routine determinations and reach high concentration values. For diagnostic purposes, the reliable correlation of pathological process (inflammation, sepsis) with the respective biomarker is of primary importance, without there being any need to know its role in the complex cascade of the endogenous substances involved in the inflammatory process.

An endogenous substance particularly suitable as a sepsis biomarker is procalcitonin. Procalcitonin is a prohormone whose serum concentrations reach very high values under the conditions of a systemic inflammation of infectious aetiology (sepsis), whereas it is virtually undetectable in healthy persons. High values of procalcitonin are also reached in a relatively early stage of a sepsis, so that the determination of procalcitonin is also suitable for early diagnosis of a sepsis and for early distinguishing of a sepsis caused by infection from severe inflammations which have other causes. The determination of procalcitonin as a sepsis marker is the subject of the publication by M. Assicot et al., "High serum procalcitonin concentrations in patients with sepsis and infection", The Lancet, Vol. 341, No. 8844, 1993, 515–518; and the patents DE 42 27 454 C2 and EP 0 656 121 B1 and U.S. Pat. No. 5,639,617. Reference is hereby made to said patents and to early literature references mentioned in said publication for supplementing the present description. In recent years, the number of publications on the subject of procalcitonin has greatly increased. Reference is therefore also made to W. Karzai et al., "Procalcitonin—A New Indicator of the Systemic Response to Severe Infection", Infection, Vol. 25, 1997, 329–334; and M. Oczenski et al., "Procalcitonin: a new parameter for the diagnosis of bacterial infection in the peri-operative period", European Journal of Anaesthesiology 1998, 15, 202–209; and furthermore H. Redl et al., "Procalcitonin release patterns in a baboon model of trauma and sepsis: Relationship to cytokines and neopterin", Crit Care Med 2000, Vol. 28, No. 11, 3659–3663; and H. Redl et al., "Non-Human Primate Models of Sepsis", in: Sepsis 1998; 2:243–253; and the further literature references cited therein, as typical of recent published reviews.

The availability of the sepsis marker procalcitonin has given considerable impetus to sepsis research, and intensive efforts are now being made to find further biomarkers which can supplement the procalcitonin determination and/or are capable of providing additional information for purposes of fine diagnosis or differential diagnosis. The search for potential new sepsis biomarkers is however complicated by the fact that frequently very little or nothing is known about the exact function or about the exact reasons for the occurrence of certain endogenous substances which are involved in inflammatory or septic processes.

The results of the experimental testing of a fruitful purely hypothetical approach to the determination of further potential sepsis markers are to be found in DE 198 47 690 A1 and WO 00/22439. There, it is shown that, in the case of sepsis, not only is the concentration of the prohormone procalcitonin increased but also significantly increased concentrations can be observed for other substances which may be included among the peptide prohormones. While the phenomenon described is well documented, the causes of the increase in the concentrations of prohormones in sepsis are still substantially unexplained.

In the present application, results of another, purely experimental approach in the search for further inflammation- or sepsis-specific biomolecules are now reported. These experimental investigations, too, originate in the determination of procalcitonin in relation to systemic inflammatory reactions of infectious aetiology. Thus, it had been observed at a very early stage that the procalcitonin is evidently not formed in the same manner in sepsis as when it is a precursor for the hormone calcitonin. Thus, high procalcitonin levels were also observed in patients whose thyroid had been removed. The thyroid therefore cannot be the organ in which procalcitonin is formed or secreted during sepsis. In the publications by H. Redl et al., "Procalcitonin release patterns in a baboon model of trauma and sepsis: Relationship to cytokines and neopterin", Crit Care Med 2000, Vol. 28, No. 11, 3659–3663; and H. Redl et al., "Non-Human Primate Models of Sepsis", Sepsis 1998; 2:243–253, the results of experimental investigations which are said to be intended for explaining the formation of procalcitonin in sepsis are reported. In said works, an artificial sepsis is produced by endotoxin administration to primates (baboons), and the experimentally produced states in which the highest procalcitonin concentrations in the blood are reached are determined. A further development of the experimental animal model described in said works serves, in the context of the present application, for determining novel endogenous sepsis-specific biomarkers of a peptic or protein nature, the occurrence of which is characteristic for sepsis or certain forms of sepsis and which therefore permit a specific diagnosis of sepsis. The primate model was chosen because of the very great similarity of the physiology of primates and humans and the high cross-reactivity with many therapeutic and diagnostic human reagents.

Since the endogenous substances formed during inflammations are part of the complex reaction cascade of the body, not only are such substances also of diagnostic interest but attempts are currently also being made, with considerable effort, to intervene therapeutically in the inflammatory process by influencing the formation and/or the concentration of individual substances of this type, in order to stop as early as possible the systemic spread of the inflammation, which spread is observed, for example, during sepsis. In this context, endogenous substances which have been shown to be involved in the inflammatory process are also regarded as potential therapeutic targets. Attempts based on certain mediators of the inflammatory process and intended to have a positive therapeutic influence on said process are described, for example, in E. A. Panacek, "Anti-TNF strategies", Journal für Anästhesie und Intensivbehandlung"; No. 2, 2001, 4–5; T. Calandra et al., "Protection from septic shock by neutralization of macrophage migration inhibitory factor", Nature Medicine, Vol. 6, No. 2, 2000, 164–170; or K. Garber, "Protein C may be sepsis solution", Nature Biotechnology, Vol. 18, 2000, 917–918. These therapeutic approaches are intended to lower the concentrations of inflammation-promoting substances or to inhibit the formation of such substances, and to do so in particular with the use of specific antibodies (against TNF-α or MIF; cf. E. A. Panacek, "Anti-TNF strategies", Journal für Anästhesie und Intensivbehandlung; No. 2, 2001, 4–5; T. Calandra et al., "Protection from septic shock by neutralization of macrophage migration inhibitory factor", Nature Medicine, Vol. 6, No. 2, 2000, 164–170) or to increase the concentration of endogenous substances which have an inhibitory effect in the inflammation cascade (Protein C; K. Garber, "Protein C may be sepsis solution", Nature Biotechnology, Vol. 18, 2000, 917–918). The last-mentioned publication gives an overview of such attempts to have a therapeutic influence on the inflammatory process by influencing selected endogenous target molecules, which attempts have unfortunately generally met with little success to date. In view of the rather disappointing therapeutic approaches to date, there is great interest in identifying further endogenous biomolecules which are as inflammation- or sepsis-specific as possible and which, as therapeutic targets, also open up new prospects for success in fighting inflammation.

The present invention is based on the fact that the so-called calcineurin B homologous protein (CHP) can be detected in considerable concentration in primates and humans with inflammations caused by infection, in contrast to healthy subjects in which it is not found or is found only in concentrations at the analytical limit of detection, which makes this protein CHP suitable both for inflammation diagnosis/sepsis diagnosis and as a novel therapeutic target.

As will be described in more detail below in the experimental section, the invention is based on the fact that, after experimental triggering of an artificial sepsis in baboons by endotoxin administration (LPS from *Salmonella Typhimurium*) and working-up of liver tissue of the treated animals by 2D gel electrophoresis, it was possible to find CHP as a peptide or protein product which is identifiable only in the treated animals. For its identification, a novel protein spot which was found only in the case of the treated animals and, according to gel electrophoresis, has a molecular weight of about 22900±700 Dalton and an isoelectric point of about 6.2 was isolated from the electrophoresis gel and separated by trypsin digestion into fragments, which were analyzed by mass spectrometry in a manner known per se and identified by comparison with known trypsin-treated proteins.

In the mass analysis of the tryptic digestion of the novel protein spot, fragments having the following masses (m/z) were found: 1169.52; 1469.50; 1550.56; 1569.7; 1645.6; 1920.81; 2386.78. Two of the 7 masses (1169.52 and 1920.81) could not be assigned to any masses of known trypsin-treated proteins. For the remaining 5 masses, the following analysis and assignment to the known sequence of CHP resulted (cf. SEQ ID NO:6; database SWISS-PROT: Entry CA22_Human: Accession number Q99653; Lin X., Barber D. L. "A calcineurin homologous protein inhibits GTPase-stimulated na-H exchange", Proc. Natl. Acad. Sci. U.S.A. 93:12636 (1996)):

The mass 1469.50 corresponds to the sequence L-Y-S-R-F-T-S-L-D-K (SEQ ID NO:1). At the amino acid S (serine, occurs twice) and T (threonine), the sequence is modified by a phosphate group in each case. The theoretical molecular weight of this fragment is 1469.499. In the amino acid sequence of CHP (without the methionine residue additionally mentioned by Lin X., above), this sequence is found in positions 31–40.

The mass 1550.56 corresponds to the sequence K-E-T-G-F-S-H-S-Q-I-T (SEQ ID NO:2), supplemented by 2 phosphate groups. The theoretical molecular weight of this fragment is 1550.564. In the amino acid sequence of CHP (without the methionine residue additionally mentioned by Lin X., above), this sequence is found in positions 19–30.

The mass 1569.7 corresponds to the sequence T-L-A-H-F-R-P-I-E-D-N-E-K (SEQ ID NO: 3). The theoretical molecular weight of this fragment is 1569.7. In the amino acid sequence of CHP (without the methionine residue additionally mentioned by Lin X., above), this sequence is found in positions 86–98.

The mass 1645.6 corresponds to the sequence A-S-T-L-L-R-D-E-E-I-K (SEQ ID NO: 4). The theoretical molecular weight of this fragment is 1645.597. In the amino acid sequence of CHP (without the methionine residue additionally mentioned by Lin X., above), this sequence is found in positions 5–18.

The mass 2386.78 corresponds to the sequence I-I-N-A-F-F-P-E-G-E-D-Q-V-N-F-R-G-F-M-R (SEQ ID NO: 5). The theoretical molecular weight of this fragment is 2386.78. In the amino acid sequence of CHP (without the methionine residue additionally mentioned by Lin X., above), this sequence is found in positions 66–85.

According to recognized principles of interpretation, such agreement is considered to be reliable identification of the product from the protein spot as CHP. The molecular weight of CHP (194 amino acids) is 22325 Dalton.

The identification of the occurrence of CHP during sepsis in the liver is of considerable scientific, diagnostic and therapeutic interest.

The human protein CHP was described for the first time in 1996 (X. Lin and D. L. Barber, A calcineurin homologous protein inhibits GTPase-stimulated Na-H exchange, Proc. Natl. Acad. Sci. USA, 93:12631–12636, 1996) and proved to be substantially identical to the rat protein p22 described shortly beforehand in the same year as $Ca^{2+}$-binding protein (M. R. Barroso et al., A Novel $Ca^{2+}$-binding protein, p22, Is Required for Constitutive Membrane Traffic, J. Biol. Chem., 271:10183–101878, 1996). The designation calcineurin B homologous protein (CHP) indicates the great similarity of this protein to the regulatory B-subunit of calcineurin (65%). There is also a great similarity between CHP and a further $Ca^{2+}$-binding protein, calmodulin (59%).

CHP is expressed in many human tissues and proved to be an essential cofactor for the regulation of NHE1, a ubiquitously expressed $Na^+/H^+$ exchanger which, when it is activated, increases the intracellular pH, which can result in activation of the cell multiplication, cell differentiation and neoplastic transformations. The degree of phosphorylation of CHP is important for the NHE1 regulation during cell division. It has furthermore been found that a transient overexpression of CHP inhibits the serum- and GTPase-stimulated NHE1 activities.

Further investigations into the physiological role of CHP confirmed its importance for NHE regulation (T. Pang et al., Calcineurin Homologous Protein as an Essential Cofactor for $Na^+/H^+$ Exchangers, J. Biol. Chem., 276:17367–17372, 2001). They also showed that CHP inhibits calcineurin activity (X. tin et al., Inhibition of Calcineurin Phosphatase Activity by a Calcineurin B Homologous Protein, J. Biol. Chem., 274:36125–36131, 1999). This finding is of considerable interest because, inter alia, calcineurin plays an important role in T-cell activation and thus also in the triggering of an immune response. For this reason, calcineurin is also a target of the immunosuppressive pharmaceutical active substances cyclosoporin A and FK506. In the light of these results, the protein CHP proves to be a previously unrecognized endogenous inhibitor of calcineurin activity and of the activation of the immune system.

It was hitherto unknown that the physiological concentrations of CHP are significantly changed in any diseases and a determination of the CHP concentration could therefore be of interest from diagnostic points of view. There were equally few proposals for influencing the physiological CHP concentrations for achieving defined therapeutic aims.

The detection, according to the invention, of comparatively high CHP concentrations in the liver of primates in which an artificial sepsis was triggered by toxin administration, with the simultaneous impossibility of detecting CHP in otherwise completely identically treated samples of control animals, is significantly high. Since the occurrence had been observed only in the treated animals, only a relatively short time after triggering of sepsis by toxin administration, it is possible to utilize this fact for providing a promising sepsis, infection and inflammation diagnosis method by determination of CHP. Of particular interest is an apparent suitability of CHP as a prognosis marker for sepsis.

CHP can be determined by any suitable detection method, but the determination in a body fluid of a patient by an immunodiagnostic method using suitable selective antibodies appears most advantageous from practical points of view.

On the basis of the fact that it was for the first time possible to detect the increased occurrence of CHP in an experimentally triggered sepsis, the possibility of utilizing CHP for diagnostic and/or therapeutic purposes in relation to inflammations and sepsis is thus opened up. For this purpose, CHP or suitable partial peptides thereof can optionally also be prepared in a targeted manner synthetically or by genetic engineering using methods which are now part of the prior art. CHP partial peptides are optionally in marked form, and may also be required as calibrators, tracers and competitors for certain assay formats for immunodiagnostic determination and prepared for this purpose in the manner explained.

Furthermore, CHP fragments or suitable partial sequences thereof can be used, by known methods of the modern prior art, also for producing specific polyclonal and in particular monoclonal antibodies which are suitable as aids for the diagnostic determination of CHP in body fluids of a patient and/or also as potential therapeutic agents. The production of suitable monoclonal antibodies against known partial peptide sequences is now part of the general prior art and need not be described specially. Furthermore, antibody production using techniques of direct genetic immunization for the corresponding DNA should also be expressly mentioned. It is therefore within the scope of the present invention to use, for example, a cDNA of CHP or CHP fragments for the immunization, since it has been found in the past that, with the use of such immunization techniques, the spectrum of obtainable antibodies can be extended. However, known antibodies against CHP, available from third parties, may also be used.

In the immunological determination of CHP, it is possible in principle to proceed as described, for example for the selective procalcitonin determination, in P. P. Ghillani et al., "Monoclonal antipeptide antibodies as tools to dissect closely related gene products", The Journal of Immunology, Vol. 141, No. 9, 1988, 3156–3163; and P. P. Ghillani et al., "Identification and Measurement of Calcitonin Precursors in Serum of Patients with Malignant Diseases", Cancer Research, Vol. 49, No. 23, 1989, 6845–6851. Variations of the techniques described and/or further immunization techniques are available to a person skilled in the art from standard works and publications and can be applied in context.

CHP or CHP fragments having the partial sequences according to SEQ ID NO:1, SEQ ID NO:2, SEQ ID NO:4 and/or SEQ ID NO:5 or partial peptides thereof can, on the basis of the results available, serve as specific marker peptides (biomarkers) for diagnosis and for monitoring of the course of inflammations and infections (in particular of systemic infections of the sepsis type). Like the determination of procalcitonin, the determination of CHP can be effected for the early differential diagnosis and for the diagnosis and for the preparation of a prognosis, for the assessment of the severity and for the therapy-accompanying assessment of the course of sepsis and infections, in such a method the content of CHP being determined in a sample of biological fluid or of a tissue of a patient and the presence of an inflammation, of a severe infection or of a sepsis being concluded from the established presence and/or amount of CHP and the result obtained being correlated with the severity of the sepsis and possibilities for treatment and/or prospects of treatment being estimated.

CHP (or optionally DNA segments coding therefor) can, however, also be used in preventive medicine or therapy of inflammations, in particular of systemic inflammations of infectious aetiology and sepsis.

Since CHP has an immunosuppressive effect, the increased concentrations of CHP in the case of a sepsis can be interpreted as counter-regulation of the body against the excessive systemic immune reaction of the body which was observed in the case of sepsis. Supporting of this counter-reaction by external CHP administration should therefore be capable of acting in the sense of controlling the septic reaction of the body so that the diagnostic finding of increased CHP concentrations in sepsis, which is reported herein, also indicates novel therapeutic possibilities.

The observation that the physiological CHP concentrations are greatly variable as a function of external stress reactions—in the above-mentioned animal model as a result of the effect of toxins—is furthermore indicative of the fact that such changes of the concentrations of the endogenous immunosuppressant CHP also occur in physiological situations which are known to lead to an undesired weakening of the immune defence, for example in the case of local inflammations which weaken the defence of the entire organism, but also in the case of external stresses due to overwork or in the case of emotional stress. In these cases, the immunosuppression produced by CHP is undesired. The therapeutic effect takes place in such cases with the aim of lowering the physiological CHP concentration for regenerating the immune defence. In such cases, the concentration of CHP can be reduced by administering binding antibodies, or by extracorporeal removal of CHP by means of lavage of the blood or plasmapheresis by means of affinity absorption. For such purposes, it is also possible to provide drugs which contain, as the actual active substance, antibodies produced against CHP or CHP fragments and prepared for administration to patients, together with a suitable pharmaceutical carrier.

CHP will thus become a potential promising therapeutic active substance for the therapy of sepsis and similar severe inflammations.

If the CHP activity is enhanced for therapeutic purposes, those molecules which contain CHP in different posttranslationally modified form, for example in glycosylated or phosphorylated form, or in a form substituted by pharmaceutical excipients, e.g. polyethylene glycol radicals, are also to be regarded as therapeutically usable CHP materials.

The discovery and identification of CHP are described in more detail below, reference being made to the attached sequence listing and parts thereof. The figures show the following:

Figures 1A, 1B:
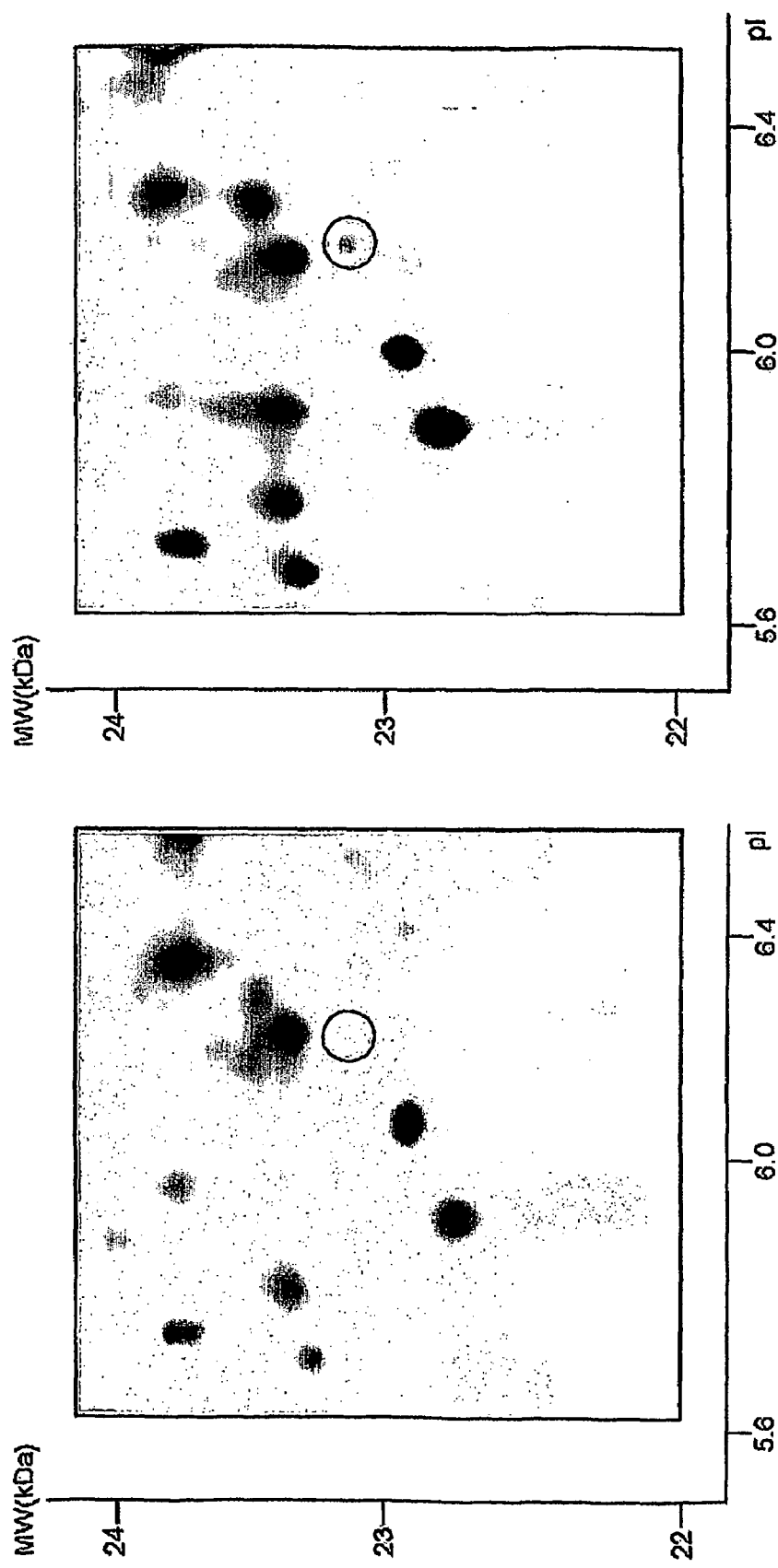
FIG. 1 shows views of 2D electrophoresis gels which permit a comparison of the spot patterns of cytoplasmic liver cell protein of a healthy baboon (A) with the liver cell proteins of a baboon 5 h after a sepsis induced by LPS administration (B). The arrow indicates the position of the sepsis-specific product according to the invention, CHP, which is distinguished in diagram (B) by a circle.
Figure 2:
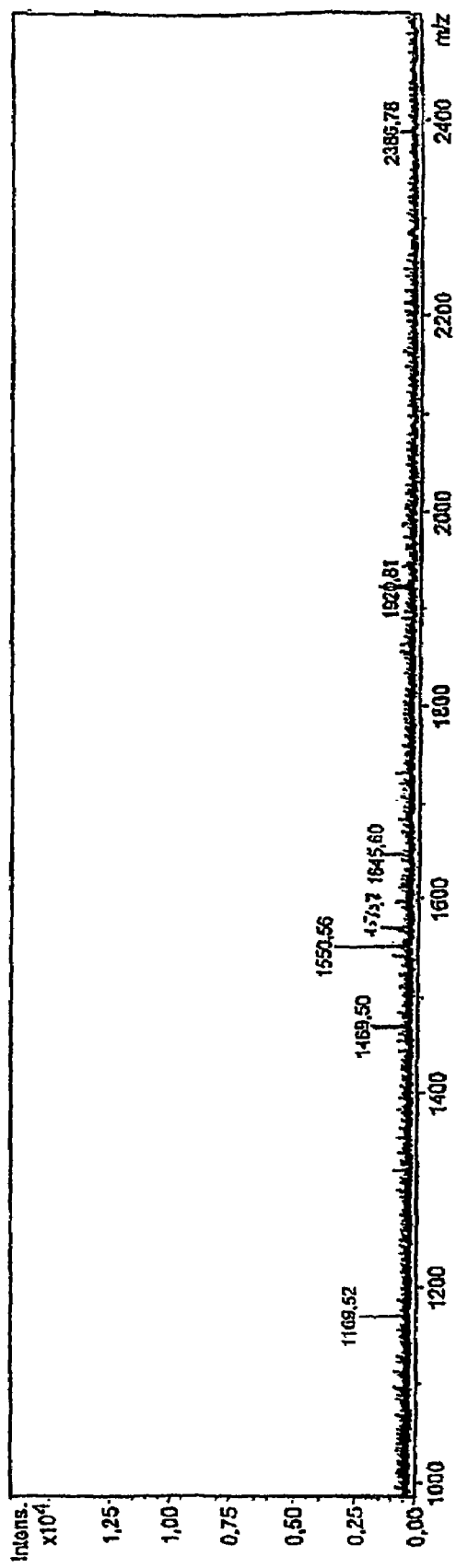
FIG. 2 shows the mass spectrum of the trypsin-digested product isolated from the gel of the 2D gel electrophoresis.

1. Infection Simulation by Endotoxin Administration in an Animal Model (Baboons).

On the basis of the experiments carried out with baboons for the stimulation of procalcitonin secretion by endotoxin injections (cf. H. Redl et al., "Procalcitonin release patterns in a baboon model of trauma and sepsis: Relationship to cytokines and neopterin", Crit Care Med 2000, Vol. 28, No. 11, 3659–3663; H. Redl et al., "Non-Human Primate Models of Sepsis", in: Sepsis 1998; 2:243–253), baboons (male, about 2 years old, weighing from 27 to 29 kg) were each intravenously administered 100 µg of LPS (lipopolysaccharide from *Salmonella Typhimurium*, source: Sigma) per kg body weight. From 5 to 5.5 h after the injection, the animals were sacrificed by intravenous administration of 10 ml of doletal. Within 60 min of their death, all organs/tissues were dissected and were stabilized by freezing in liquid nitrogen.

During the further processing, 1.5 ml of buffer A (50 mM tris/HCl, pH 7.1, 100 mM KCl, 20% of glycerol) were added to samples of the individual frozen tissues (1 g) while cooling with nitrogen, and the samples were pulverized in a porcelain mortar to give a powder (cf. J. Klose, "Fractionated Extraction of Total Tissue Proteins from Mouse and Human for 2-D Electrophoresis", in: Methods in Molecular Biology, Vol. 112: 2-D Proteome Analysis Protocols, Humana Press Inc., Totowa, N.J.). After subsequent centrifuging for 1 hour at 100,000 g and +4° C., the supernatant obtained was recovered and was stored at –80° C. until required for further processing.

Using the tissue extracts obtained in this manner, an investigation was first carried out to determine in which of the tissues investigated the largest amounts of the known sepsis biomarker procalcitonin can be produced by endotoxin administration. In the determined tissue having the highest level of procalcitonin formation, further previously unidentified protein products which occurred only after endotoxin administration were then sought by means of differential proteome analysis. For this purpose, tissue samples of untreated baboons were used as control tissue samples, the sacrificing and obtaining of samples having been effected under conditions identical to those in the case of the treated animals.

2. Determination of Baboon Tissues Having the Highest Level of Procalcitonin Formation After Endotoxin Injection.

Samples of the individual tissues were investigated with the aid of an immunoluminometric test which operates (similarly to the LU-MItest® PCT of the Applicant, developed for the determination of human procalcitonin) with, on the one hand, an antibody against baboon calcitonin, immobilized on polystyrene tubes, and a monoclonal antibody marked with an acridinium ester and directed against the N-terminus of baboon procalcitonin. With the aid of this test, the contents of baboon procalcitonin in the individual samples were determined after calibration of the test using recombinant human procalcitonin.

The experiments showed that liver tissue gives the largest amount of procalcitonin. The protein extracts from baboon liver which were obtained in the manner described at the outset were therefore used for searching for novel sepsis-specific biomarkers.

3. Proteome Analysis Using Cytoplasmic Liver Cell Proteins of Baboons.

Cytoplasmic liver cell protein extracts of, on the one hand, healthy baboons (control) and, on the other hand, baboons which had been injected with LPS were used in a proteome analysis. In the initial analytical 2D gel electrophoresis, liver extract containing 100 μg of protein was stabilized to 9M urea, 70 mM DTT, 2% ampholyte pH 2–4 and then separated by means of analytical 2D gel electrophoresis, as described in J. Klose et al., "Two-dimensional electrophoresis of proteins: An updated protocol and implications for a functional analysis of the genome", Electrophoresis 1995, 16, 1034–1059. The visualization of the proteins in the 2D electrophoresis gel was effected by means of silver staining (cf. J. Heukeshoven et al., "Improved silver staining procedure for fast staining in Phast-System Development Unit. I. Staining of sodium dodecyl gels", Electrophoresis 1988, 9, 28–32).

For evaluation, the protein spot patterns of the samples of untreated animals were compared with the protein spot patterns which resulted from liver tissue samples of treated animals. Substances which occurred in no control sample but additionally in all treated animals were selected for further analytical investigations. FIG. 1 shows a comparison of the 2D electrophoresis gels for a control sample (A) and a sample of a treated animal (B), the additional protein spot in (B) corresponding to a novel protein, the position of which is singled out by an arrow and a circle.

The novel specific proteins identified in the protein spot pattern of the analytical 2D gel electrophoresis were then prepared by means of preparatory 2D gel electrophoresis using 350 μg of protein (once again cf. (10)). In the preparative 2D gel electrophoresis, the staining was effected by means of Coomassie Brilliant Blue G250 (cf. V. Neuhoff et al., "Improved staining of proteins in polyacrylamide gels including isoelectric focusing gels with clear background at nanogram sensitivity using Coomassie Brilliant Blue G-250 and R-250", Electrophoresis 1988, 9, 255–262).

The protein spots preselected for the further analysis were cut out of the gel, using the method which is described in A. Otto et al., "Identification of human myocardial proteins separated by two-dimensional electrophoresis using an effective sample preparation for mass spectrometry", Electrophoresis 1996, 17, 1643–1650, trypsin-digested and then analyzed by mass spectroscopy, in particular with the use of mass spectrometric investigations as described and discussed, for example, in G. Neubauer et al., "Mass spectrometry and EST-database searching allows characterization of the multi-protein spliceosome complex", in: nature genetics vol. 20, 1998, 46–50; J. Lingner et al., "Reverse Transcriptase Motifs in the Catalytic Subunit of Telomerase", in: Science, Vol. 276, 1997, 561–567; M. Mann et al., "Use of mass spectrometry-derived data to annotate nucleotide and protein sequence databases", in: TRENDS in Biochemical Sciences, Vol. 26, 1, 2001, 54–61. After an ESI (ElectroSprayIonization), the trypsin-digested samples were subjected to tandem mass spectrometry. A Q-TOF mass spectrometer having a so-called nanoflow-Z-Spray ion source from Micromass, UK, was used. The procedure corresponded to the working instructions of the equipment manufacturer.

4. Identification of CHP

As shown in FIGS. 1(A) and 1(B), liver cell extracts of baboons to which an LPS injection had been administered contained, inter alia, a spot of a protein for which a molecular weight of about 22,900±700 Dalton was estimated on the basis of the gel electrophoresis data in comparison with marker substances of known molecular weight, while an isoelectric point of 6.1 to 6.3 was determined from the relative position of the protein from the first dimension.

In the mass analysis of the tryptic digestion of the novel protein spot, fragments having the following masses (m/z) were found: 1169.52; 1469.50; 1550.56; 1569.7; 1645.6; 1920.81; 2386.78. Two of the 7 masses (1169.52 and 1920.81) could not be assigned to any masses of known trypsin-treated proteins. For the remaining 5 masses, the following analysis and assignment to the known sequence of CHP were obtained (cf. SEQ ID NO:6; Nice Prot View of SWISS-PROT: Entry CA22_Human; Accession number Q99653; Lin X., Barber D. L. "A calcineurin homologous protein inhibits GTPase-stimulated na-H exchanger", Proc. Natl. Acad. Sci. U.S.A. 93:12636 (1996)):

The mass 1469.50 corresponds to the sequence L-Y-S-R-F-T-S-L-D-K (SEQ ID NO:1). At the amino acid S (serine, occurs twice) and T (threonine), the sequence is modified by a phosphate group in each case. The theoretical molecular weight of this fragment is 1469.499. In the amino acid sequence of CHP (without the methionine residue additionally mentioned by Lin X., above), this sequence is found in positions 31–40.

The mass 1550.56 corresponds to the sequence K-E-T-G-F-S-H-S-Q-I-T (SEQ ID NO:2), supplemented by 2 phosphate groups. The theoretical molecular weight of this fragment is 1550.564. In the amino acid sequence of CHP (without the methionine residue additionally mentioned by Lin X., above), this sequence is found in positions 19–30.

The mass 1569.7 corresponds to the sequence T-L-A-H-F-R-P-I-E-D-N-E-K (SEQ ID NO: 3). The theoretical molecular weight of this fragment is 1569.7. In the amino acid sequence of CHP (without the methionine residue additionally mentioned by Lin X., above), this sequence is found in positions 86–98.

The mass 1645.6 corresponds to the sequence A-S-T-L-L-R-D-E-E-I-K (SEQ ID NO: 4). The theoretical molecular weight of this fragment is 1645.597. In the amino acid sequence of CHP (without the methionine residue additionally mentioned by Lin X., above), this sequence is found in positions 5–18.

The mass 2386.78 corresponds to the sequence I-I-N-A-F-F-P-E-G-E-D-Q-V-N-F-R-G-F-M-R (SEQ ID NO: 5). The theoretical molecular weight of this fragment is 2386.78. In the amino acid sequence of CHP (without the methionine residue additionally mentioned by Lin X., above), this sequence is found in positions 66–85.

According to recognized principles of interpretation, such agreement is considered to be reliable identification of the product from the protein spot as CHP. The molecular weight of CHP (194 amino acids) is 22325 Dalton.

The increased CHP concentrations found for the first time permits its use as a novel biomarker for sepsis and inflammations, in particular infectious inflammations.

The same discovery for the first time also suggests a therapeutic use of CHP, in particular as an active substance for having an inhibiting effect on the septic reaction of the body by administration of CHP. The invention consequently also relates to pharmaceutical compositions which contain CHP as the actual active substance, together with a suitable pharmaceutical carrier, or those which are aimed at lowering the physiological CHP concentrations in certain pathological processes, for example those compositions which contain, as the actual active substance, antibodies against CHP or CHP fragments or processed CHP, for example CHP phosphorylated in a certain form, such antibodies preferably being prepared, for example humanized, for administration to patients and moreover being present together with a suitable pharmaceutical carrier.

The invention claimed is:

1. A method for diagnosis of sepsis in a patient suspected of having sepsis, comprising testing a tissue sample from said patient for the presence of calcineurin B homologous protein (CHP), wherein a higher amount of said CHP in said sample compared to a control group is indicative of sepsis.

2. Method according to claim 1, wherein the presence of said CHP is determined by an immunodiagnostic method of determination.

3. Method according to claim 2, wherein CHP is determined using an antibody that specifically binds to a CHP fragment comprising the sequence of SEQ ID NO: 1, SEQ ID NO: 2, SEQ ID NO: 4 or SEQ ID NO: 5.

* * * * *

```
                        SEQUENCE LISTING

<160> NUMBER OF SEQ ID NOS: 6

<210> SEQ ID NO 1
<211> LENGTH: 10
<212> TYPE: PRT
<213> ORGANISM: Primat (Pavian)

<400> SEQUENCE: 1

Leu Tyr Ser Arg Phe Thr Ser Leu Asp Lys
 1               5                  10

<210> SEQ ID NO 2
<211> LENGTH: 12
<212> TYPE: PRT
<213> ORGANISM: Primat (Pavian)

<400> SEQUENCE: 2

Lys Glu Thr Gly Phe Ser His Ser Gln Ile Thr Arg
 1               5                  10

<210> SEQ ID NO 3
<211> LENGTH: 13
<212> TYPE: PRT
<213> ORGANISM: Primat (Pavian)

<400> SEQUENCE: 3

Thr Leu Ala His Phe Arg Pro Ile Glu Asp Asn Glu Lys
 1               5                  10

<210> SEQ ID NO 4
<211> LENGTH: 14
<212> TYPE: PRT
<213> ORGANISM: Primat (Pavian)

<400> SEQUENCE: 4

Ala Ser Thr Leu Leu Arg Asp Glu Glu Leu Glu Glu Ile Lys
 1               5                  10

<210> SEQ ID NO 5
<211> LENGTH: 20
<212> TYPE: PRT
<213> ORGANISM: Primat (Pavian)

<400> SEQUENCE: 5

Ile Ile Asn Ala Phe Phe Pro Glu Gly Glu Asp Gln Val Asn Phe Arg
 1               5                  10                  15

Gly Phe Met Arg
            20

<210> SEQ ID NO 6
```

```
-continued

<211> LENGTH: 194
<212> TYPE: PRT
<213> ORGANISM: Homo sapiens
<300> PUBLICATION INFORMATION:
<301> AUTHORS: Lin, Xia
<302> TITLE: A calcineurin homologous protein inhibits
      GTPase-stimulated Na-H exchange
<303> JOURNAL: Proc. Natl. Acad. Sci. U.S.A.
<304> VOLUME: 1996
<305> ISSUE: vol.93
<306> PAGES: 12631-12636

<400> SEQUENCE: 6

Gly Ser Arg Ala Ser Thr Leu Leu Arg Asp Glu Glu Leu Glu Glu Ile
 1               5                  10                  15

Lys Lys Glu Thr Gly Phe Ser His Ser Gln Ile Thr Arg Leu Tyr Ser
                20                  25                  30

Arg Phe Thr Ser Leu Asp Lys Gly Glu Asn Gly Thr Leu Ser Arg Glu
                35                  40                  45

Asp Phe Gln Arg Ile Pro Glu Leu Ala Ile Asn Pro Leu Gly Asp Arg
            50                  55                  60

Ile Ile Asn Ala Phe Phe Pro Glu Gly Glu Asp Gln Val Asn Phe Arg
 65                 70                  75                  80

Gly Phe Met Arg Thr Leu Ala His Phe Arg Pro Ile Glu Asp Asn Glu
                85                  90                  95

Lys Ser Lys Asp Val Asn Gly Pro Glu Pro Leu Asn Ser Arg Ser Asn
                100                 105                 110

Lys Leu His Phe Ala Phe Arg Leu Tyr Asp Leu Asp Lys Asp Glu Lys
            115                 120                 125

Ile Ser Arg Asp Glu Leu Leu Gln Val Leu Arg Met Met Val Gly Val
        130                 135                 140

Asn Ile Ser Asp Glu Gln Leu Gly Ser Ile Ala Asp Arg Thr Ile Gln
145                 150                 155                 160

Glu Ala Asp Gln Asp Gly Asp Ser Ala Ile Ser Phe Thr Glu Phe Val
                165                 170                 175

Lys Val Leu Glu Lys Val Asp Val Glu Gln Lys Met Ser Ile Arg Phe
                180                 185                 190

Leu His
```